(12) United States Patent
Katagiri

(10) Patent No.: US 9,040,767 B2
(45) Date of Patent: May 26, 2015

(54) RESIN VOLUME REDUCTION PROCESSING SYSTEM AND RESIN VOLUME REDUCTION PROCESSING METHOD

(75) Inventor: Gen-ichi Katagiri, Yokohama (JP)

(73) Assignee: FUJI ELECTRIC CO., LTD., Kawasaki-shi (JP)

( * ) Notice: Subject to any disclaimer, the term of this patent is extended or adjusted under 35 U.S.C. 154(b) by 284 days.

(21) Appl. No.: 13/640,419

(22) PCT Filed: Feb. 6, 2012

(86) PCT No.: PCT/JP2012/052586
§ 371 (c)(1),
(2), (4) Date: Dec. 19, 2012

(87) PCT Pub. No.: WO2012/111463
PCT Pub. Date: Aug. 23, 2012

(65) Prior Publication Data
US 2013/0090512 A1    Apr. 11, 2013

(30) Foreign Application Priority Data
Feb. 15, 2011   (JP) .................................. 2011-029829

(51) Int. Cl.
G21F 9/30   (2006.01)
G21F 9/32   (2006.01)
A61L 2/24   (2006.01)

(52) U.S. Cl.
CPC ..... *G21F 9/307* (2013.01); *G21F 9/30* (2013.01); *G21F 9/32* (2013.01); *A61L 2/24* (2013.01)

(58) Field of Classification Search
CPC ............. G21F 9/30; G21F 9/307; G21F 9/32; A61L 2/24

USPC ................................................ 588/7
See application file for complete search history.

(56) References Cited

U.S. PATENT DOCUMENTS

| | | | | |
|---|---|---|---|---|
| 4,671,898 A | * | 6/1987 | Hultgren ........................... | 588/3 |
| 4,732,705 A | * | 3/1988 | Laske et al. ....................... | 588/3 |
| 5,877,225 A | * | 3/1999 | Blinn et al. ...................... | 521/28 |

FOREIGN PATENT DOCUMENTS

| | | | |
|---|---|---|---|
| JP | 06-034796 A | | 2/1994 |
| JP | 2001-153998 A | | 6/2001 |
| JP | 2001-305287 | * | 10/2001 |
| JP | 2010-078578 A | | 4/2010 |
| WO | WO92/03829 | * | 3/1992 |

\* cited by examiner

*Primary Examiner* — David M Brunsman
(74) *Attorney, Agent, or Firm* — Rabin & Berdo, P.C.

(57) ABSTRACT

The cost relating to a reduction in volume and storage of a waste resin including a radioactive nuclide is reduced. In an aspect of the invention, a volume reduction processing system 1000 is provided. The volume reduction processing system 1000 includes a radioactivity meter 102 that measures the radioactivity of a processing target resin, a volume reduction processing device 110 that carries out a heating process, and an oxidation process using oxygen plasma P on the processing target resin, and a process stopping point computation unit 180 that determines a process stopping point for carrying out a volume reduction process on the processing target resin with the volume reduction processing device as far as a volume reduction target value. The volume reduction processing device 110 stops at least one process of the heating process and oxidation process on the process stopping point being reached.

18 Claims, 7 Drawing Sheets

RESIN VOLUME REDUCTION PROCESSING SYSTEM AND RESIN VOLUME REDUCTION PROCESSING METHOD

This application is a 371 filing of PCT/JP2012/052586, filed Feb. 6, 2012.

TECHNICAL FIELD

The present invention relates to a resin volume reduction processing system and resin volume reduction processing method. More particularly, the invention relates to a volume reduction processing system and a volume reduction processing method that reduce the volume of spent ion-exchange resin used mainly in a nuclear power generation facility, or the like.

BACKGROUND ART

In recent years, there has been an increase in the importance of disposal technology for disposing of waste matter generated during the operation of a nuclear power generation facility, or waste matter generated as the result of decommissioning a reactor. In order to reduce the cost incurred in, for example, the control, stocking, or controlled disposal of a spent ion-exchange resin (hereafter called a "processing target resin") used in a nuclear power generation facility, processing target resin volume reduction process technology has been developed. To date, a volume reduction process has been carried out on the processing target resin using a method whereby, for example, a radioactive nuclide is separated from the processing target resin, and the processing target resin is burned together with combustible waste matter, or the like. However, a processing target resin for which burning is not appropriate has been temporarily stored by, for example, stocking on the premises of a nuclear power generation facility. A volume reduction processing device utilizing oxygen plasma is disclosed in, for example, Patent Document 1 (JP-A-2001-153998) as a method for reducing the volume of this kind of processing target resin.

A high volume reduction ratio is achieved with the volume reduction processing device disclosed in Patent Document 1. That is, with a processing using the volume reduction processing device disclosed in Patent Document 1, the volume of the processing target resin is reduced at a high volume reduction ratio by combining a process breaking down or carbonizing the processing target resin with heat and a process oxidizing or ashing gas generated by the breakdown or the carbonized processing target resin, using oxygen plasma. To give a numerical example confirmed by the inventor of the application, with the method disclosed in Patent Document 1, when measuring a mass when moisture is removed from the processing target resin by dripping (a drained standard mass), and contrasting it with the mass of a solid matter forming a residue after volume reduction (hereafter called a "residual solid matter"), it is possible to reduce the volume of the processing target resin to in the region of, for example, one-twentieth. As a result of this, even when fabricating a mortar-like solidified waste by sealing the residual solid matter by mixing it with, for example, cement, there is no noticeable decrease in the strength of the solidified waste, which is also true of mortar including a fine aggregate such as sand. Because of this, there is an advantage in that it is possible to load a greater amount of the residual solid matter within the range of a strength standard provided for the solidified waste, that is, a solidified waste standard strength condition, which leads to a reduction in disposal expenses. Moreover, when employing the method disclosed in Patent Document 1, it is possible to carry out volume reduction with the radioactive nuclide allowed to remain in the residual solid matter.

RELATED ART DOCUMENTS

Patent Documents

Patent Document 1: JP-A-2001-153998

OUTLINE OF THE INVENTION

Problems to be Solved by the Invention

However, it is not the case that such a high volume reduction ratio as that described in Patent Document 1 is always necessary in an actual radioactive waste matter disposal method. For example, there is also carried out a disposal of a waste body whose control level is lowered by manufacturing a waste body wherein a small amount of residual waste matter is mixed into cement. Also, it is not the case that the kind of method whereby the residual solid matter after the reduction in volume of the processing target resin accompanying a radioactive substance is sealed with cement, as heretofore described, is always employed. For example, there is also the kind of case in which, by sealing using a resin, the residue is hardened and disposed of. In these examples, it is not the case that the heretofore described high volume reduction ratio in the region of one-twentieth is necessary.

Also, it should also be noted that in an actual handling of storing the residual solid matter after a volume reduction, classes (hereafter called "storage classes") categorized in accordance with the amount of radioactivity (radioactivity concentration) per unit volume of the stored residual solid matter are set depending on the country or region, and a control level standard, that is, a standard of control strictness, is fixed for each storage class. With a volume reduction process premised on this kind of storage, it is desirable that a volume reduction process of an extent commensurate with the objective storage class category is carried out. In particular, when a volume reduction process is carried out on the processing target resin at an excessively high volume reduction ratio, and the radioactivity concentration due to the residual radioactivity of the residual solid matter is high, the residual solid matter may fall under a storage class applied to waste matter with a high radioactivity concentration. In this kind of case, as there arises a duty to store the residual solid matter in conformity with a storage level standard for stricter storage, the cost for storage increases.

The invention, having an object of solving at least some of these problems, contributes to a low cost operating of a nuclear power generation facility by enabling a volume reduction process whose total cost is reduced when considering storage cost too.

Means for Solving the Problems

The inventor of the application has focused on the idea that the total cost incurred by the heretofore described volume reduction process and subsequent storage can be reduced by employing a radioactivity meter in the volume reduction process, and aborting or stopping the volume reduction process at an appropriate timing. That is, in one aspect of the invention, there is provided a volume reduction processing system including a radioactivity meter that measures the radioactivity of a processing target resin accompanying a radioactive substance, and outputs radioactivity data or a radioactivity signal indicating the value of the radioactivity, a volume reduction processing device that carries out a volume reduction process on the processing target resin by carrying out a heating process on the processing target resin, and carrying out an oxidation process on at least one, or both, of the processing target resin itself and gas emitted from the processing target resin using oxygen plasma, and a process stopping point computation unit that determines a process stopping point for carrying out a volume reduction process on the processing target resin with the volume reduction processing device as far as a volume reduction target value, based on the volume reduction target value and the radioactivity data or radioactivity signal, wherein the volume reduction processing device stops at least one process of the heating process and oxidation process on the process stopping point being reached.

Herein, the total cost refers to a cost which is the total of the processing cost as far as processing a certain unit processing volume of the processing target resin (a batch) to the residual solid matter after the volume reduction process and the storage cost incurred in storing the residual solid matter. Of these, all of various kinds of temporary or transient cost arising in accordance with the processing, such as energy costs, machine costs, and transportation costs, are included in the processing cost. The processing cost generally increases the more the residual solid matter obtained from the same unit processing amount of processing target resin is reduced, that is, the more the volume reduction ratio is increased. Also, all arbitrary costs incurred over the whole of the storage period are included in the storage cost. The storage cost is generally fixed for each storage class categorized in accordance with the radioactivity, that is, the radioactivity concentration, per unit volume of the residual solid matter. The storage cost decreases further the more the volume reduction ratio of the processing target resin is increased in the same storage class. Also, in a storage class of a higher radioactivity concentration, the storage cost increases in accordance with the need for storing at a stricter control level compared with that of a storage class of a low radioactivity concentration.

The radioactivity meter includes any measuring instrument that measures any radiation, this being $\alpha$ rays, $\beta$ rays, and $\gamma$ rays. Among these, it is possible to include a radioactivity meter having energy resolution that can measure, for example, in each $\gamma$ ray energy. The radioactivity meter, for example, outputs radioactivity data or a radioactivity signal corresponding to the radioactivity of the ray type or energy used in the storage class category. Although radioactivity is normally measured with becquerels (Bq) or curies (Ci) as units, any form expressed by information that can be converted into radioactivity is included in the radioactivity data or radioactivity signal.

The volume reduction processing device refers to any device that can carry out the kind of process wherein a heating process is carried out on the processing target resin, and an oxidation process is carried out on at least one, or both, of the processing target resin itself and gas emitted from the processing target resin, using oxygen plasma.

The process stopping point computation unit is, for example, a functional means or a processing means realized as a computer that carries out a processing action in accordance with a program so as to carry out a predetermined processing.

The volume reduction target value is, for example, an arbitrary numerical index that can specify to what extent the volume of the processing target resin has been reduced, and is set as a target value for the processing. The volume reduction target value, for example, may be specified by the volume reduction ratio, or can also be specified by a weight reduction ratio.

The process stopping point is any information that can be used for determining the timing at which the processing is stopped, and includes any value that can specify the timing using, for example, a value of some physical mass, a value indicating a processing stage, a value indicating time, or the like. A typical process stopping point is determined in accordance with the weight reduction ratio of the processing target resin, an accumulation value of the concentration of carbon containing gas (carbon dioxide, carbon monoxide, or the like), or the time for the process. Herein, the process stopping point is determined based on the reduction volume target value and the radioactivity data or radioactivity signal. It is the process stopping point computation unit realized by the computer as a functional means or a processing means that executes the computation.

The invention can also be implemented as a volume reduction processing method. That is, in one aspect of the invention, there is provided a volume reduction processing method including a step of a radioactivity meter measuring the radioactivity of a processing target resin accompanying a radioactive substance, and outputting radioactivity data or a radioactivity signal indicating the value of the radioactivity, a step of a volume reduction processing device carrying out a volume reduction process on the processing target resin by carrying out a heating process on the processing target resin, and carrying out an oxidation process on at least one, or both, of the processing target resin itself and gas emitted from the processing target resin using oxygen plasma, a step of a process stopping point computation unit determining a time needed for processing or a process stopping time adopted as a process stopping point for carrying out a volume reduction process on the processing target resin with the volume reduction processing device as far as a volume reduction target value, based on the volume reduction target value and the radioactivity data or radioactivity signal, and a step of the volume reduction processing device stopping at least one process of the heating process and oxidation process on the process stopping point being reached.

In both of the heretofore described aspects of the invention, it is preferable that the volume reduction target value is determined in accordance with a storage class for disposing of or storing the residual solid matter of the processing target resin.

Advantage of the Invention

According to either of the heretofore described aspects of the invention, for example, it is possible to carry out a volume reduction process of an extent that does not lead to a rise in storage cost, and thus possible to realize a volume reduction process whose total cost is reduced.

MODE FOR CARRYING OUT THE INVENTION

Figure 1:
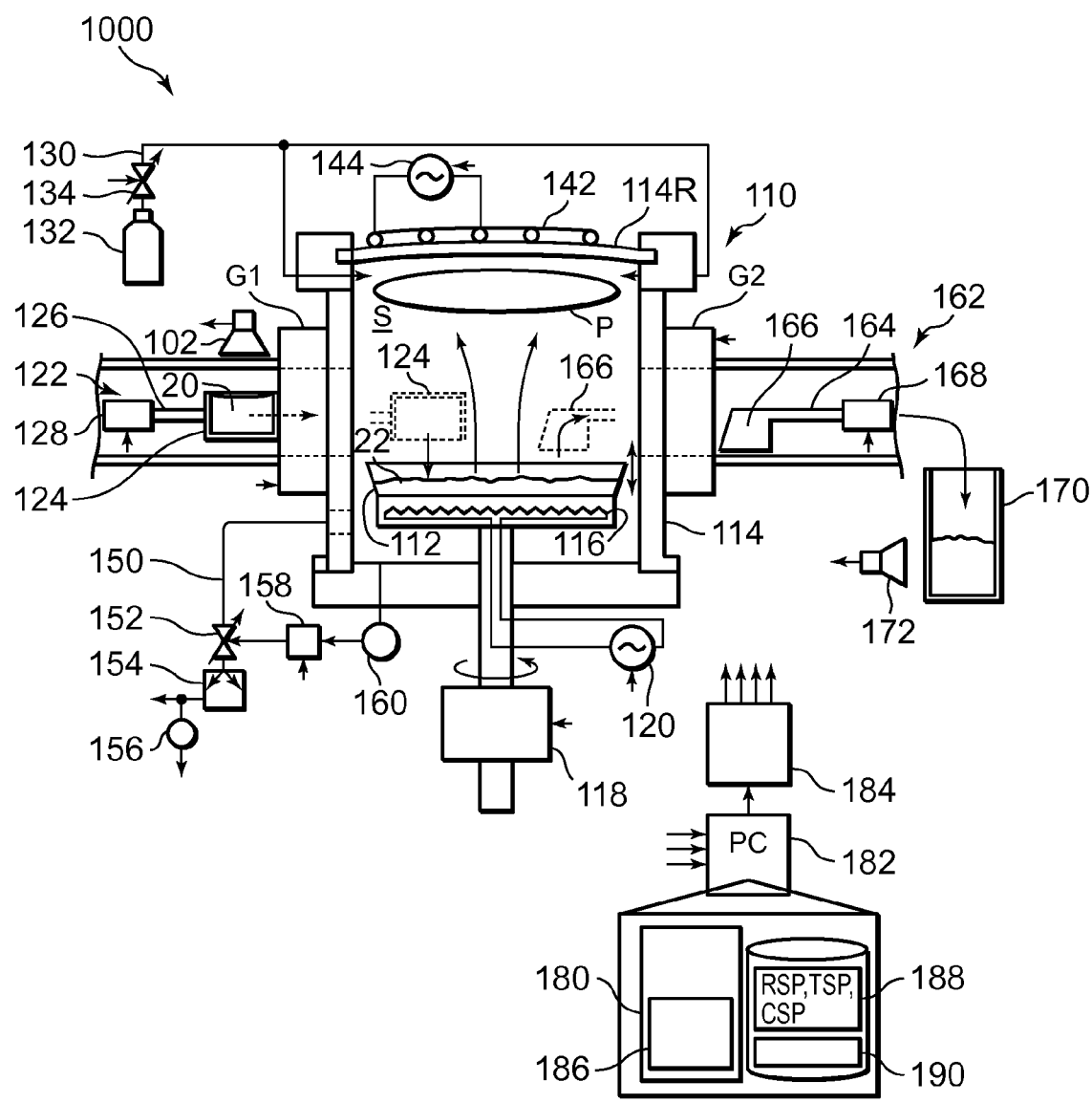
FIG. 1 is a schematic sectional view showing a configuration of a volume reduction processing system in an embodiment of the invention.

Hereafter, a description will be given of an embodiment of the invention. In the following description, the same reference numerals and signs are given to portions or components common to all the drawings, unless otherwise stated. Also, it is not necessarily the case that all the components of an embodiment are shown maintaining scale with respect to each other in the drawings.

First Embodiment

1 System Configuration

FIG. 1 is a schematic sectional view showing a configuration of a volume reduction processing system 1000 in a first embodiment of the invention. A radioactivity meter 102, a volume reduction processing device 110, and a process stopping point computation unit 180 are included in the volume reduction processing system 1000.

Of these, the radioactivity meter 102 is an arbitrary radioactivity meter that measures the radioactivity of a processing target resin 20 before the processing target resin 20 is supplied to the volume reduction processing device 110. A semiconductor detector that measures γ rays through energy resolution can be included as a typical radioactivity meter 102. The radioactivity meter 102 outputs radioactivity data or a radioactivity signal indicating the value of the radioactivity of the processing target resin 20, which is the processing target. When the radioactivity meter 102 is a radioactivity meter having γ ray energy resolving capability, it is possible, while identifying a radioactive nuclide from, for example, the γ ray energy emitted, to measure the radioactivity in the identified nuclide. The disposition of the radioactivity meter 102 not being limited to the position shown in FIG. 1, it is disposed in any position wherein it is possible to acquire the value of the radioactivity of the processing target resin 20, which is the processing target.

Also, the volume reduction processing device 110 includes, inside a vacuum receptacle 114, a stage 112 on which is placed the supplied processing target resin 20 (a processing target resin 22). A configuration of the volume reduction processing device 110, and an action thereof, will be described in detail hereafter.

The processing target resin 20 is supplied through a supply side gate valve G1 to the stage 112 by a supply mechanism 122. In order to carry out the supply action, the supply mechanism 122 includes a metering box 124 fabricated to a predetermined capacity. In order to supply the processing target resin 20, firstly, the metering box 124 is delivered by an arm 126 through the opened supply side gate valve G1 to a position in a space above the stage 112. Next, by causing the metering box 124 to rotate around the shaft of the arm 126 in this position, the processing target resin 20 inside the metering box 124 is caused to drop onto the upper surface of the stage 112. A metering box drive mechanism 128 that enables this kind of action is connected to the arm 126.

The stage 112 is fabricated in a circular dish form, and is a metal tray on the upper surface of which the processing target resin 22 can be placed. A heater 116 is provided in the interior of a flat plate portion of the stage 112 on which the processing target resin 22 is placed, and the temperature of the stage 112 itself can be raised using the heater 116. The stage 112 is configured so that, while maintaining the air tightness of the vacuum receptacle 114, a rotating action is possible around a shaft passing through the center of the circular dish and perpendicular to the flat plate portion. A drive mechanism 118 can cause the stage 112 to carry out a slow rotating action, for example, in the region of once every few minutes to a few times every minute. Also, the stage 112 is fabricated so that a position of the stage 112 in the up-down direction of the drawing in FIG. 1, that is, the height of the stage 112, can be changed by an unshown drive mechanism. A heating power source 120 that supplies controlled power to the heater 116 is connected to the stage 112. In order to control temperature, a temperature sensor (not shown) that measures the temperature of the stage 112 itself is installed in the stage 112. The power supplied to the heater 116 is controlled in accordance with a temperature measurement signal from the temperature sensor. Although not particularly limited, the temperature of the stage 112 can be controlled to a temperature of, for example, 400° C. or 700° C., appropriate for a volume reduction process.

The volume reduction processing device 110 includes the vacuum receptacle 114 fabricated in a cylindrical form on the whole. A gas supply line 130 for supplying oxygen to an internal space of the vacuum receptacle 114 is connected to the vacuum receptacle 114. Oxygen from an oxygen canister 132 is supplied from the gas supply line 130, through a regulator valve 134, to the internal space of the vacuum receptacle 114 at a controlled flow rate. Also, a high frequency coil 142 is disposed on the outer surface on the atmosphere side of a top wall 114R of the vacuum receptacle 114.

The high frequency coil 142 is a coil wherein a linear member such as, for example, copper is formed in a spiral form. The high frequency coil 142 has connection portions in a central portion and peripheral portion of the spiral form. The high frequency coil 142 is used in order to excite plasma in a space on the inner side of the top wall 114R of the vacuum receptacle 114, that is, in a space S above the stage 112. For this reason, a high frequency power source 144 of a frequency appropriate for inductive coupling with the plasma is connected to the high frequency coil 142. As the plasma is excited while oxygen is supplied, the plasma is mainly oxygen plasma. Also, an insulating body is adopted as the top wall 114R of the vacuum receptacle 114 in order to generate a high frequency electromagnetic field caused by the high frequency coil 142 in the space S. Speaking most plainly, the top wall 114R is fabricated of fused silica glass. The configuration and disposition of a high frequency coil that can be employed in the embodiment are not particularly limited to the disposition of the high frequency coil 142. For example, it is possible to implement the volume reduction process of the embodiment by using a high frequency coil of any form and disposition appropriate to exciting oxygen plasma.

An exhaust line 150 for maintaining the interior in a depressurized condition is also connected to the vacuum receptacle 114. An exhaust valve 152 and a vacuum pump 154 are connected to the exhaust line 150. The degree of opening of the exhaust valve 152 being controlled by a pressure control unit 158, the pressure control unit 158 continuously carries out pressure control based on a signal from a pressure sensor 160 that measures the pressure in the internal space of the vacuum receptacle 114. The pressure control unit 158 automatically controls the pressure of the vacuum receptacle 114 as an APC (Automatic Pressure Controller) that controls the exhaust valve 152 based on a signal from the pressure sensor 160.

A carbon dioxide sensor 156 is connected to an exit side path of a vacuum pump 154. Concentration data or a concentration signal in accordance with the concentration of carbon dioxide gas measured in an exhaust path from the vacuum receptacle 114 is output from the carbon dioxide sensor 156. In the embodiment, in place of the carbon dioxide sensor 156, it is possible to use any kind of gas sensor that achieves the object of measuring the concentration of carbon containing gas. For example, the same object is also achieved by using a carbon monoxide sensor rather than a carbon dioxide sensor. Furthermore, a gas sensor such as the carbon dioxide sensor 156 may be installed, for example, on a side wall of the vacuum receptacle 114, or in the path of the exhaust line 150 up to the vacuum pump 154, rather than in the exit side path of the vacuum pump 154.

A volume reduction process is carried out on the supplied processing target resin 20 (the processing target resin 22) in a condition in which it is placed on the stage 112. The volume reduction process is carried out by a heating process using the stage 112 and an oxidation process using oxygen plasma P. That is, the volume reduction processing device 110 carries out a heating process on the processing target resin 22, and carries out an oxidation process on at least one, or both, of the processing target resin 22 itself and gas emitted from the processing target resin 22, using the oxygen plasma P. Details of this process will be described hereafter.

On the volume reduction process being carried out, a solid (residual solid matter) is obtained, in a condition in which it is placed on the stage 112, from the processing target resin 22. Because of this, after the process is finished, the residual solid matter is removed from the stage 112 by an ejection mechanism 162, and ejected to the exterior of the vacuum receptacle 114. For the sake of the ejection, an ejection side gate valve G2 is attached to the vacuum receptacle 114. Also, a suction pipe 164 including a recovery nozzle 166 is disposed in the ejection mechanism 162. The suction pipe 164 is connected to an ejection drive mechanism 168 for driving the position of the recovery nozzle 166, in a condition in which the ejection side gate valve G2 is opened, to a position appropriate for suctioning the residual solid matter on the stage 112. The residual solid matter suctioned by the suction pipe 164 is recovered while preventing scattering using a bag filter or cyclone (neither shown) for recovering the residual solid matter from an air flow, and temporarily stored in a residual solid matter receptacle 170. An extra radioactivity meter 172 for measuring the radiation finally remaining in the residual solid matter is included in the residual solid matter receptacle 170. The residual solid matter in the residual solid matter receptacle 170 is subsequently sealed in, for example, cement or resin, thereby increasing safety, transported to an appropriate facility such as, for example, a final disposal site, and semi-permanently stored, that is, disposed of.

The extra radioactivity meter 172 outputs the radioactivity actually exhibited by the residual solid matter as residual radiation data or a residual radiation signal. Because of this, the residual radiation data or residual radiation signal output by the extra radioactivity meter 172 can be used for determining the storage class of the residual solid matter.

The process stopping point computation unit 180 is a functional means mounted as a program in, for example, a computer 182. The function of the process stopping point computation unit 180 is a function that determines a process stopping point for carrying out a volume reduction process as far as a volume reduction target value on the processing target resin 20 using the volume reduction processing device 110. When deciding on the process stopping point, a computation is carried out based on the volume reduction target value, and on radioactivity data or a radioactivity signal obtained by the radioactivity meter 102. Then, the determined process stopping point is stored in a process stopping point storage unit 188. The volume reduction processing device 110 is controlled by the computer 182 in which the process stopping point computation unit 180 is mounted, or by a sequence control unit 184. Under this control, the volume reduction processing device 110 stops at least one of the heating process and the oxidation process on the process stopping point being reached. The computer 182 in which the process stopping point computation unit 180 is mounted executes control based on, for example, the value of the process stopping point of the process stopping point storage unit 188. Alternatively, the computer 182 transmits a control signal to the sequence control unit 184, causing the sequence control unit 184 to execute the same kind of control.

Herein, the computer 182 in which the process stopping point computation unit 180 is mounted receives data or a signal from the volume reduction processing device 110, the radioactivity meter 102, the carbon dioxide sensor 156, and the extra radioactivity meter 172. Also, the computer 182, for example, controls an action of the volume reduction processing device 110 directly, or via the sequence control unit 184. The stage drive mechanism 118, heating power source 120, metering box drive mechanism 128, regulator valve 134, high frequency power source 144, pressure control unit 158, ejection drive mechanism 168, supply side gate valve G1, and ejection side gate valve G2 are included in components of the volume reduction processing device 110 that receive a control by the computer 182 directly, or via the sequence control unit 184. The pressure control unit 158, at the same time as the pressure control unit 158 itself acts so as to even out the pressure of the interior of the vacuum receptacle 114 using the pressure sensor 160 and control of the exhaust valve 152, may also receive a control by the sequence control unit 184, and change a pressure command value, which is a pressure control target value.

The process stopping point computation unit 180 further has an accumulator unit 186 that calculates an accumulation value wherein at least any ones of concentration values converted from concentration data and concentration signals from the carbon dioxide sensor 156 are accumulated. The accumulator unit 186 is a functional means realized utilizing a computing function of the computer 182. The accumulator unit 186 executes a computation that temporally accumulates concentration data or concentration signals from the carbon dioxide sensor 156 in accordance with carbon dioxide gas concentration. An accumulation value thereof is an accumulation value from the initial period until a point in the processing, indicating the total amount of carbon dioxide gas (carbon containing gas) emitted from the processing target resin 22 and measured by the carbon dioxide sensor 156. The process stopping point computation unit 180 receives an accumulation value output by the accumulator unit 186, and utilizes the accumulation value in order to determine how much carbon containing gas has been emitted from the processing target resin 22 up to that point. An accumulation value of carbon containing gas, such as carbon dioxide, emitted is utilized as an index indicating to what extent the processing target resin 20 volume reduction process has progressed, as described hereafter.

2 Outline of Volume Reduction Processing System Processing Action

Next, a description will be given, with further reference to the drawings, of a processing using the volume reduction processing system 1000. FIG. 2(*a*) shows a graph of indices (temperature and carbon dioxide concentration) indicating the condition of the volume reduction processing system 1000, and FIG. 2(*b*) shows a graph of an estimated weight reduction ratio indicating the state of resin volume reduction. The indices shown in FIG. 2(*a*) as indices of the condition of the volume reduction processing system 1000 are the temperature of the stage 112 (a curve 202) and the value of the carbon dioxide concentration obtained from the carbon dioxide sensor 156 (a curve 204). Also, what is shown in FIG. 2(*b*) is an estimated weight reduction ratio (a curve 214) wherein the state of resin volume reduction is estimated.

The temperature of the stage 112 indicated by the curve 202 is the temperature indication value indicated by the temperature sensor (not shown) installed in the stage 112, and is shown on the vertical axis with numerals as indicators. As opposed to this, the curve 204 indicating the carbon dioxide concentration value output by the carbon dioxide sensor 156 indicates only temporal behavior, and the graduations of the value are arbitrary units. However, the carbon dioxide concentration value indicated by the curve 204 is plotted linearly, and is described so that the horizontal axis is a concentration of zero. The horizontal axis of FIG. 2 is a time whose measurement is started from the moment at which a first sub-batch (first sub-batch) of the processing target resin 22 is placed on the stage 112 and the supply side gate valve G1 is closed, that is, a processing time. All of the processes shown in FIG. 2(*a*) take a time of approximately 24 hours. A sub-batch is a processing unit wherein a batch of the processing target resin 20 forming a unit processing amount in a series of volume reduction processes is further subdivided. In the description of the embodiment, one batch of the processing target resin 20 is processed divided into first to fourth sub-batches in one portion of the process, and processed as the original one batch in the remainder of the process.

A description based on FIG. 2(*a*) is a description of a method of carrying out a volume reduction process as high as possible, with an object of aiding understanding of the processing using the volume reduction processing system 1000 of the embodiment. In the embodiment, this corresponds to a case of executing a volume reduction process without setting a process stopping point, or a case of executing a volume reduction process so that a volume reduction ratio as high as possible is obtained by setting a process stopping point such that the process progresses sufficiently. A situation wherein the process is aborted or stopped at an appropriate point utilizing a process stopping point is also included in the embodiment of the invention.

As shown in FIG. 2(*a*), a volume reduction process using the volume reduction processing system 1000 is broadly divided into two processing phases, that is, a first phase (first process) and a second phase (second process). In the first phase, the stage 112 is heated to approximately 400° C., while in the second phase, the stage 112 is heated to approximately 700° C. These temperatures exhibit a more detailed temporal fluctuation, as indicated by the curve 202. Herein, for example, when the processing target of the volume reduction processing system 1000 is an ion-exchange resin utilized by a nuclear power generation facility, or the like, the processing target resin 22 is a mixture of the ion-exchange resin, a radioactive substance accompanying the ion-exchange resin, and residual moisture. Also, an ion-exchange resin utilized by a nuclear power generation facility accompanies a radioactive substance including a radioactive isotope by the radioactive substance being adsorbed to or held by the ion-exchange resin itself in the form of ions or a corrosion product (cladding).

An outline of the process in each of the heretofore described phases will be described hereafter. Firstly, in the first phase, a carbonization process is carried out by heating the processing target resin 22. This process is the first process carried out on the processing target resin 22. On being placed on the stage 112 and heating being started, the processing target resin 22 emits a large amount of water vapor by the time it reaches a temperature of about 400° C., and also emits a cracked gas owing to a detachment and breakdown of lower molecules of an anion-exchange group, or the like. Subsequently, when the temperature rises sufficiently to around 400° C., the processing target resin 22 further emits a cracked gas owing to a detachment and breakdown of higher components caused by a breakdown of a resin base material. The emission of these cracked gases is similar to a phenomenon of a common organic substance emitting a cracked gas owing to heat. In this condition, power for exciting the plasma P by inductive coupling is supplied to the high frequency coil 142. Consequently, the emitted cracked gases are oxidized by the oxygen plasma P excited in the space above the stage 112. Because of this, components in the cracked gases liable to be oxidized, for example, carbon components, are oxidized. Carbon dioxide or carbon monoxide is included in a gas generated by the cracked gases being oxidized by the oxygen plasma P, that is, an exhaust gas. The exhaust gas is exhausted via the exhaust line 150. Breakdown in this process is intense immediately after the start of the process, and starts to weaken after continuing for a certain amount of time. This corresponds to a component broken down at that temperature being consumed. A substance in which carbonization has progressed is left on the stage 112 after the cracked gas components are emitted from the processing target resin 22. This carbonized processing target resin 22, even when sufficiently processed in the first phase, progresses only as far as a carbonized condition. Because of this, carbon components remain in the processing target resin 22 at this point. In this way, by combining the heating of the stage 112 and the oxidation using the oxygen plasma P, the processing target resin 22 breakdown process, the carbonization process, and the cracked gas oxidation process are executed in the first phase.

The carbon components of the cracked gases in the first phase are exhausted from the exhaust line 150 as carbon dioxide or carbon monoxide gas in the oxidized exhaust gas, and the concentration thereof is measured by the carbon dioxide sensor 156. The carbon dioxide concentration of the first phase rises along with the rise of the temperature in each sub-batch and, after a high value is maintained for a certain time, drops as broken down components are consumed. The carbon dioxide concentration value is a direct index indicating the amount of carbon oxidized per unit time in the processing target resin 22. On top of this, the carbon dioxide concentration value is also an indirect index to all components oxidized in the processing target resin 22. All components oxidized in the processing target resin 22 may include, other than carbon components, nitrogen components, sulfur components, and hydrogen components.

In the first phase, the processing target resin 22 is processed with sub-batches, wherein the processing target resin 22 is sub-divided to the processing capability range of the volume reduction processing device 110, as units. An aspect of a case wherein the processing target resin 22 is divided into four sub-batches and is introduced thereinto is shown in FIG. 2(*a*). In the first phase, the state of progress of the carbonization and breakdown processes owing to the heating of the first sub-batch of the processing target resin 22 is monitored via the carbon dioxide concentration value. Then, when it is determined from the carbon dioxide concentration value that the processing of the first sub-batch has progressed to a certain extent, the supply side gate valve G1 is opened, and the processing target resin 22 of the next sub-batch, that is, the second sub-batch, is additionally introduced. At this time, a residual solid matter on which processing has progressed still remains on the stage 112 as the first sub-batch. The processing target resin 22 of the second sub-batch is supplied to the stage 112 in this condition. Consequently, the newly introduced second sub-batch, and the first sub-batch which is partway processed, of the processing target resin 22 are both processed. Thereafter, the third sub-batch and fourth sub-batch are also processed in the same way. The reason why the first phase is implemented with the processing target resin 22 sub-divided in this way is that a large amount of cracked gas is emitted from the processing target resin 22 in the first phase in comparison with that in the processing in the second phase, and it may happen that the cracked gas processing capability is insufficient.

Next, a description will be given of the second phase. When shifting from the first phase to the second phase, the vacuum receptacle 114 remains depressurized, without being opened to the atmosphere. However, the pressure, that is, the degree of vacuum, is changed between the first phase and second phase. The processing target of the second phase is a semi-processed substance left on the stage 112, carbonized by passing through the processing in the first phase as the first to fourth sub-batches of the processing target resin 22. Herein, the semi-processed substance too is referred to as the processing target resin 22. In the second phase, the temperature of the stage 112 is raised to 700° C. in this condition. When the temperature of the processing target resin 22 carbonized by the processing of the first phase rises, the oxygen plasma acts on the carbonized processing target resin 22, and the carbon component is removed by oxidation. That is, the second phase is a further volume reduction process wherein the carbon component of the carbonized processing target resin 22 is reduced by an ashing wherein a heating process and oxygen plasma are combined. The oxygen plasma P is used in the second phase too, in the same way as in the first phase. For this reason, power for exciting the plasma P by inductive coupling is supplied to the high frequency coil 142. However, while oxidation of the cracked gases is an action expected of the oxygen plasma P in the first phase, the oxygen plasma P is excited in the second phase in expectation of an action ashing the carbonized processing target resin 22. In order to differentiate between the expected actions, conditions for exciting the oxygen plasma P generally differ between the first phase and second phase. Most typically, a higher pressure is selected for the oxygen plasma exciting conditions in the second phase than in the first phase. Also, the oxygen supply direction is selected so that the airflow from the top wall 114R toward the stage 112 is greater in the second phase compared with that in the first phase.

When the processing target resin 22 is ashed in the second phase, the carbon component or the like, remaining in the processing target resin 22 becomes an exhaust gas like a carbon dioxide or carbon monoxide gas, and is emitted from the exhaust line 150. The carbon dioxide concentration in the second phase also rises along with the rise of the temperature and, after a high value is maintained for a certain time, drops in accordance with the consumption of oxidized components. In the second phase too, in the same way as in the first phase, the carbon dioxide concentration value obtained from the carbon dioxide sensor 156 is a direct index indicating the amount of carbon oxidized per unit time in the processing target resin 22, and is also an indirect index to all components oxidized in the processing target resin 22.

Of the processing shown in FIG. 2(*a*), the processing in the second phase is such that the processing is continued until the carbon dioxide concentration obtained from the carbon dioxide sensor 156 reaches zero. That is, it is the graph of FIG. 2(*a*) that shows a process of processing until the components removed by oxidation from the processing target resin 22 under the conditions of the second phase run out. At a point at the right end of the graph of FIG. 2(*a*), substances finally remaining in the processing target resin 22 are a metal oxide including a radioactive nuclide, and a slight amount of carbon component that cannot be removed under the conditions of the second phase. Because of this, when the processing in the second phase is completed, a residual solid matter in a condition wherein it has been subjected to the volume reduction process to an extent that the volume thereof cannot practically be reduced any further is left on the stage 112.

It is the graph of FIG. 2(*b*) that shows, using the estimated weight reduction ratio, how the volume of the processing target resin 22 is reduced as a result of the progress of this kind of processing. The curve 214 shown in the graph is an estimated value estimated from the accumulation value of the carbon dioxide concentration at each stage indicating the state of volume reduction. Also, the extent of volume reduction is estimated using the extent of reduction in mass (weight), that is, the weight reduction ratio, rather than the reduction in volume. In order to estimate the estimated weight reduction ratio, calculation is carried out in the following way. The total mass of the batches (first to fourth sub-batches) forming the processing unit of the processing target resin 20, which is the processing target, is measured in advance. As the mass is a mass including moisture, the mass of the water is subtracted from the mass of the processing target resin 20 using a separately measured moisture regain, thus determining the dry mass. Of the dry mass of the processing target resin 20 in the unprocessed condition, mass subjected to the volume reduction process, other than the mass of the carbon components, is the mass of oxidized components—those being nitrogen components, sulfur components, and hydrogen components—in the event that they exist. Consequently, the weight reduction ratio at each point can be obtained as $$(1 - \text{mass of residual solid matter at each point}/\text{dry mass}) \times 100\% \quad \text{Expression (1)}$$

Herein, in order to simplify the description, the weight reduction ratio is described with only a definition using the dry mass. Instead of using the dry mass, it is also possible to obtain the weight reduction ratio with another definition, such as a definition using a mass including moisture.

In the case of the processing described thus far, in particular in the processing shown in FIG. 2(*a*), processing is carried out inside the vacuum receptacle 114. Because of this, it is after the processing in the second phase is completed that it is actually possible to measure the mass of the residual solid matter in accordance with Expression (1). That is, the weight reduction ratio is finally obtained after the second phase is completed, using the mass of the residual solid matter suctioned by the ejection mechanism 162, and temporarily stored in the residual solid matter receptacle 170. Because of this, it is actually difficult to obtain the weight reduction ratio at each point in Expression (1).

However, according to the studies by the inventor of the application, despite various kinds of component—those being carbon components, nitrogen components, sulfur components, and hydrogen components—being removed by oxidation, it is possible to estimate the volume reduction ratio partway through the processing with a certain degree of accuracy by controlling focusing only on the carbon components. To conclude, the estimated weight reduction ratio at each point can be expressed as $k \times$ accumulation value of carbon containing gas concentration/dry mass $\times 100\%$    Expression (2)

Figure 2A:
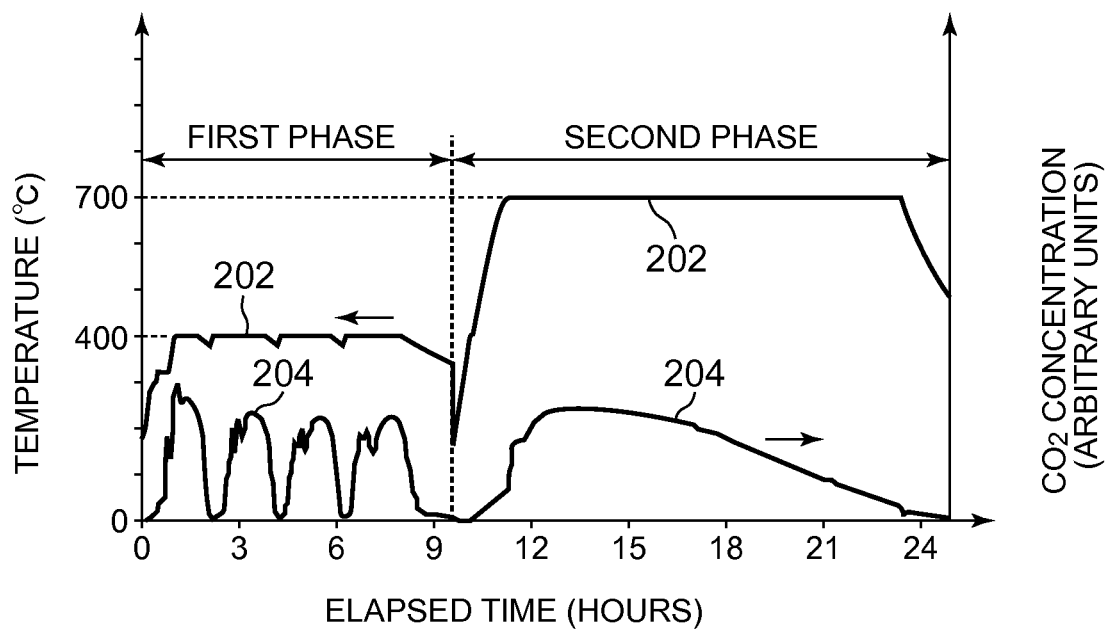
FIG. 2($a$) is a graph of indices (temperature and carbon dioxide concentration) indicating the condition of the volume reduction processing system in an embodiment of the invention, and FIG. 2($b$) is a graph of an estimated weight reduction ratio indicating the state of resin volume reduction.
Figure 2B:
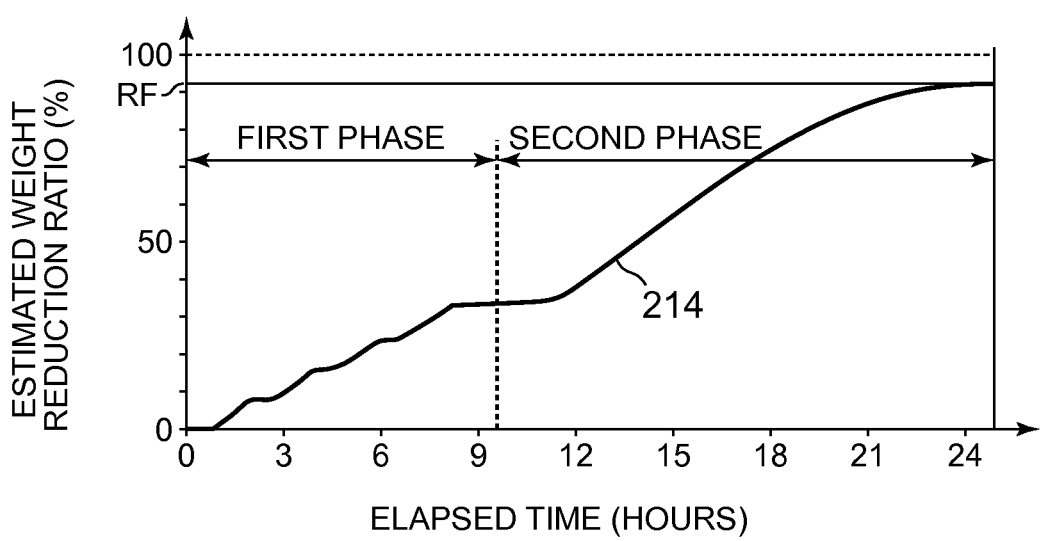

Here, the accumulation value of carbon containing gas concentration is an accumulation value wherein the value of measured carbon dioxide shown by the carbon dioxide sensor 156 is accumulated along with time when using the carbon dioxide sensor 156 of FIG. 1, and k is a proportionality coefficient. In order to determine k, it is sufficient to determine in such a way that the volume reduction process is executed until carbon containing gas ceases to be emitted, as shown in FIGS. 2(a) and (b), and the values of Expression (1) and Expression (2) at the final point of the process are equal. In FIG. 2(b), the weight reduction ratio obtained from the mass of the residual solid matter discharged after the processing is continued until the concentration of carbon containing gas reaches zero is shown as a mark RF. The curve 214 of FIG. 2(b) is plotted with the final value of the accumulation value of the carbon containing gas concentration coinciding with the mark RE 2-1 Process Stopping Action Thus far, a description has been given of a method of carrying out a volume reduction process as high as possible. When carrying out an actual processing, however, an action such as to abort or stop the processing at an appropriate timing, taking into consideration the storage class category, is efficient.

2-2 Cost when Storage Class Category does not Change

Figure 3A:
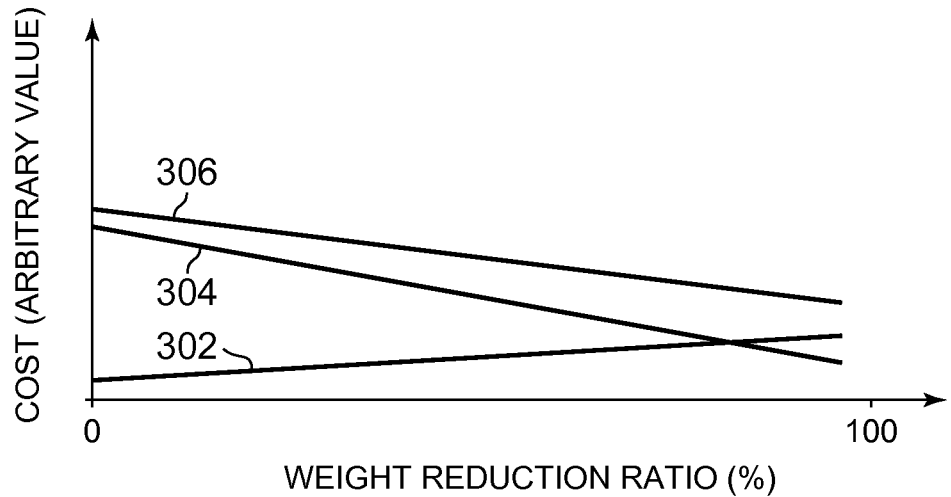
FIGS. 3($a$) and 3($b$) show explanatory diagrams showing aspects of processing cost and storage cost shifting with respect to weight reduction ratio in an embodiment of the invention.
Figure 3B:
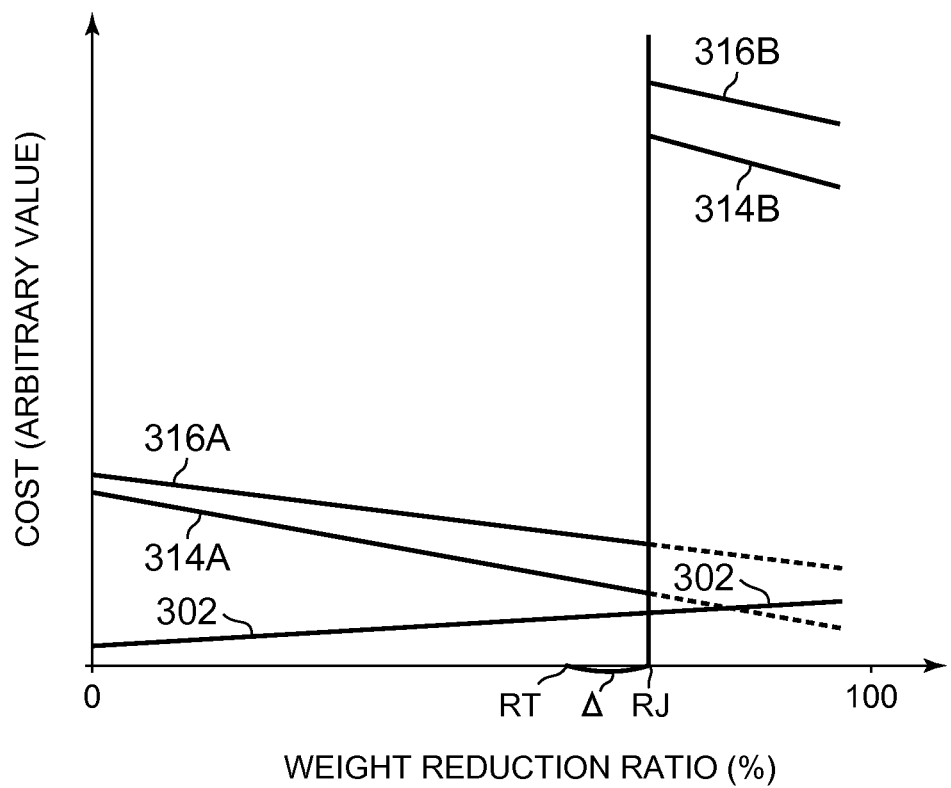

In FIG. 3, explanatory diagrams showing aspects of processing cost and storage cost shifting with respect to weight reduction ratio, are shown. Of these, FIG. 3(a) shows a case in which the storage class does not change with respect to weight reduction ratio, while FIG. 3(b) shows a case in which the storage class changes with respect to weight reduction ratio. A straight line 302 in FIG. 3(a), showing the processing cost of the volume reduction process, is shown as a straight line that rises in accordance with the weight reduction ratio being raised. Meanwhile, a straight line 304 shows the storage cost incurred in the storage of the residual solid matter. The storage cost of the residual solid matter decreases more the higher the weight reduction ratio rises, within a range in which the storage class does not change. Consequently, when the storage class does not change, the total cost decreases more the higher the weight reduction ratio rises, as shown by a straight line 306, which is the sum of the straight line 302 and straight line 304.

2-3 Cost when Storage Class Category Changes

Herein, when, for example, the carbon components decrease and the reduction in resin volume progresses when carrying out the volume reduction process, it may happen that the radioactivity value per unit volume, that is, the radioactivity concentration (activity concentration), increases, and the storage class becomes the next high concentration storage class. When looking at the actual processing cost, the cost for storing in conformity with regulations imposed on waste matter of the high concentration storage class soars to, for example, ten times or the like in comparison with that of the low concentration storage class. Straight lines 314A and 314B in FIG. 3(b) show this with divided straight lines. When this kind of jump in the storage cost occurs, the sum of the storage cost and the volume reduction process processing cost of the straight line 302, naturally, is as in divided straight lines 316A and 316B, and a jump also occurs in the total cost with respect to the weight reduction ratio. In this case, it is preferable that the volume reduction process is aborted or stopped before a weight reduction ratio value at which the total cost discontinuously jumps. That is, a value a certain leeway $\Delta$ smaller than a value of a weight reduction ratio RJ, at which a discontinuous jump occurs in the total cost, is set as a volume reduction target value. This is a volume reduction target value RT of FIG. 3(b).

2-4 Process Stopping Point Based on Volume Reduction Target Value

The actual storage class category is determined in accordance with the radioactivity concentration. Because of this, even in the event that there are residual solid matters obtained from volume reduction processes at the same weight reduction ratio, when the initial radioactivity concentration values of the processing target resin 22 differ, there is a possibility that the residual solid matters will be classified into separate storage classes. That is, in order to determine the weight reduction ratio RJ of FIG. 3(b) at which a discontinuous jump occurs in the total cost, it is necessary to compute the value of the weight reduction ratio at which a discontinuous jump occurs in the total cost from both the radioactivity concentration that forms the boundary value for the classification into storage classes and the initial radioactivity concentration of the processing target resin 22 measured by the radioactivity meter 102. By using the computed value, it is possible, after determining the weight reduction ratio RJ at which a discontinuous jump occurs in the cost, to decide the volume reduction target value RT as the heretofore described weight reduction ratio smaller by the leeway $\Delta$.

Figure 4A:
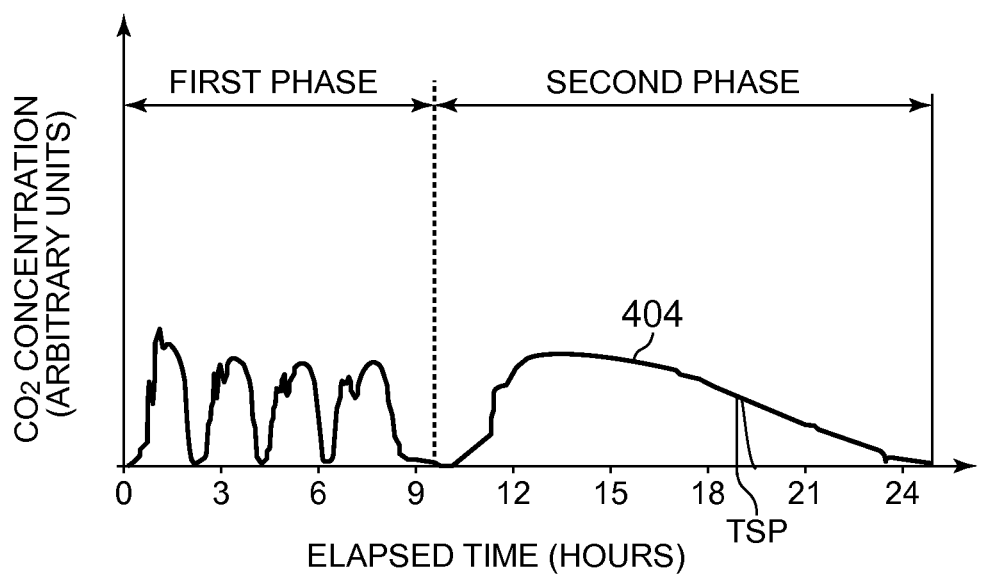
FIGS. 4(a) and 4(b) show graphs showing an aspect of processing progress when a volume reduction target value is provided in an embodiment of the invention.
Figure 4B:
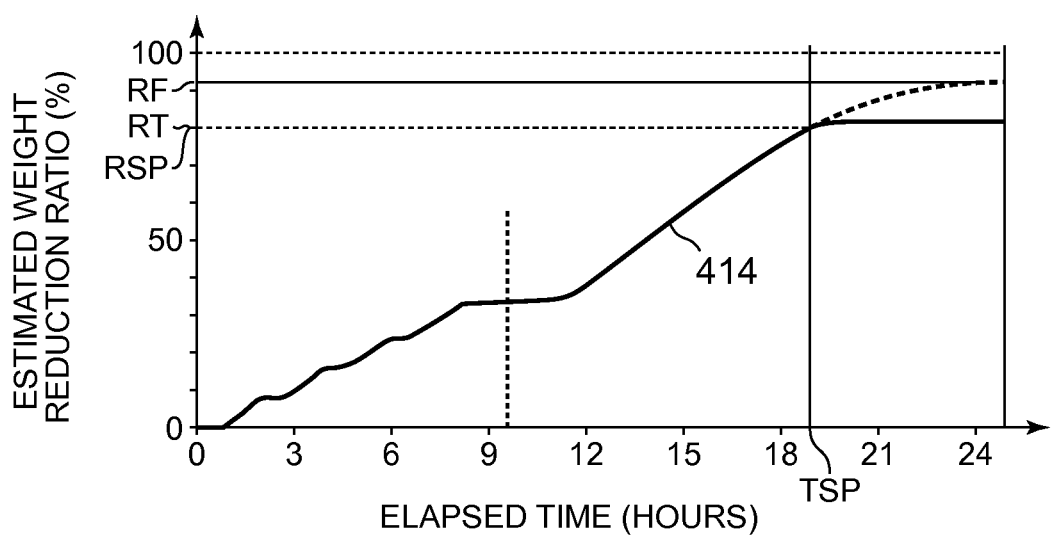

Once the volume reduction target value RT is determined, the process stopping point computation unit 180 (FIG. 1), using the volume reduction target value RT, executes a process determining a process stopping point. Then, a stopping of the processing by the volume reduction processing device 110 is carried out in accordance with the process stopping point. FIG. 4 shows graphs of an aspect of processing progress when the volume reduction target value RT is provided. FIG. 4(a) is a graph showing a temporal change in carbon dioxide concentration in the volume reduction process, in the same way as is shown in FIG. 2(a). The accumulation value of carbon dioxide gas concentration is a value wherein carbon dioxide gas concentrations from the start to each point in the processing are accumulated. The value is converted to an estimated volume reduction ratio in accordance with Expression (2). The converted estimated volume reduction ratio is shown in FIG. 4(b). FIG. 4(b) is a graph showing a temporal change in estimated weight reduction ratio in the volume reduction process, in the same way as is shown in FIG. 2(b). Herein, the volume reduction target value RT is shown in FIG. 4(b) as a value on the vertical axis.

Because of this, provided that the process stopping point computation unit 180 monitors the processing progress by carrying out a calculation of Expression (2) at each point utilizing the accumulation value from the accumulator unit 186, it is possible to determine the process stopping point. The determination process is carried out in various ways, in accordance with a measurement value fixing the process stopping point or a kind of physical amount.

Firstly, the process stopping point is typically determined as a weight reduction ratio of the processing target resin, an accumulation value of a carbon containing gas such as carbon dioxide or carbon monoxide, a time needed for processing, or a process stopping time. Of these typical examples, a process stopping point when specified by the weight reduction ratio of the processing target resin is referred to as a weight reduction ratio process stopping point RSP. Most typically, the volume reduction target value RT (FIG. 3(*b*)) itself is selected as the weight reduction ratio process stopping point RSP, as shown in FIG. 4(*b*). In this case, the value of the weight reduction ratio process stopping point RSP is stored as it is in the process stopping point storage unit 188. As a similar example, a value a certain leeway smaller than the volume reduction target value RT may be adopted as the weight reduction ratio process stopping point RSP.

As another typical example, there is a case in which the process stopping point is determined in accordance with the accumulation value of carbon containing gas. This process stopping point is referred to as a carbon process stopping point CSP (not shown). The carbon process stopping point CSP is most typically taken to be an accumulation value of carbon containing gas to which the volume reduction target value RT (FIG. 3(*b*)) is provided. Consequently, the carbon process stopping point CSP is easily calculated as the accumulation value of carbon containing gas when Expression (2) is taken to be equivalent to the volume reduction target value RT. On the process stopping point computation unit 180 executing the computation, the carbon process stopping point CSP is stored in the process stopping point storage unit 188. In Modification Example 1, to be described hereafter, a description will be given of a method of more accurately determining the carbon process stopping point CSP.

As still another typical example, there is a case in which the process stopping point is determined as the time needed for processing or the process stopping time. This process stopping point is referred to as a time process stopping point TSP. The time process stopping point TSP is most typically taken to be a processing time to which the volume reduction target value RT (FIG. 3(*b*)) is provided, as shown in FIG. 4(*b*). In order to determine the time process stopping point TSP from the volume reduction target value RT, it is necessary that the curve 214 (FIG. 2(*b*)) is obtained in advance. In order to do this, the mark RF is determined in advance by carrying out a processing until the end using a resin sample of the same kind as the processing target resin 20, thus obtaining the curve 214 of FIG. 2(*b*), and the curve 214 is stored in an arbitrary storage means as a calibration curve between the processing time and weight reduction ratio. Subsequently, by retrieving the stored calibration curve, it is possible to determine the time process stopping point TSP to which the volume reduction target value RT is provided. On the process stopping point computation unit 180 executing the computation, the time process stopping point TSP is stored in the process stopping point storage unit 188.

In this way, the process stopping point can be determined in various ways. Also, whichever process stopping point is employed, it is possible to determine the process stopping point by setting an arbitrary leeway. Every process stopping point is determined based on the volume reduction target value RT, and on radioactivity data or a radioactivity signal.

The process stopping point determined by the process stopping point computation unit 180, that is, the weight reduction ratio process stopping point RSP, carbon process stopping point CSP, or time process stopping point TSP, is preferably set so as to be positioned in a period during which the second phase (second process) is being carried out. This is because, while there is still a large amount of carbon remaining in the first phase (first process), in which the carbonization process is carried out, the processing has progressed sufficiently in the stage of the second phase, and the process stopping point is unlikely to cause any impediment to the subsequent disposal, that is, the semi-permanent storage.

A curve 404 of FIG. 4(*a*) is the value of the carbon dioxide concentration obtained from the carbon dioxide sensor 156, while a curve 414 of FIG. 4(*b*) is an estimated weight reduction ratio wherein the state of resin volume reduction is estimated. As shown in FIG. 4, when the processing reaches the process stopping point and is stopped, the carbon dioxide concentration decreases sharply from that point, and an increase in the estimated weight reduction ratio is no longer observed. That is, the processing stops soon. For the sake of comparison, a curve in a case in which no process stopping point is utilized (FIG. 2(*a*)) is shown as a chain line in FIG. 4(*a*). Herein, the stopping of the processing is most typically such that the heating process using the heater 116 is stopped, and the oxidation process using the oxygen plasma P is stopped. Also, the stopping of the oxidation process is carried out by stopping the supply of oxygen from the gas supply line 130, and stopping the supply of power by the high frequency power source 144. However, in the embodiment, it is possible to execute an arbitrary stopping process by which the progress of the volume reduction process is stopped. In particular, as there is little emission of cracked gas, and the ashing of the processing target resin 22 is the main process, in the processing in the second phase, it is possible to end the volume reduction process simply by executing either one of the stopping of the heating process using the heater 116 and the stopping of the oxidation using the oxygen plasma P.

Figure 5:
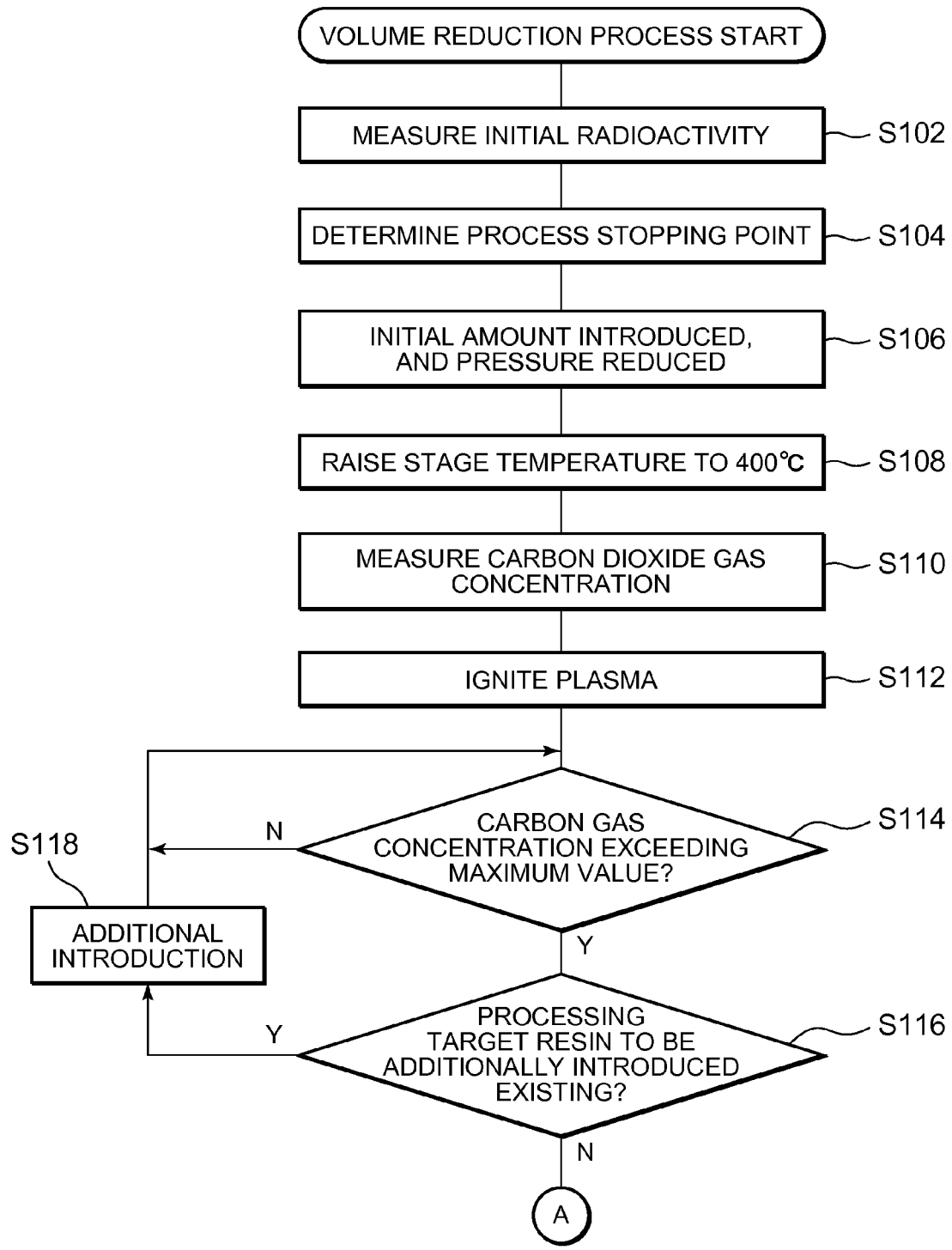
FIG. 5 is a flowchart illustrating a volume reduction processing action implemented by the volume reduction processing system of an embodiment of the invention.
Figure 6:
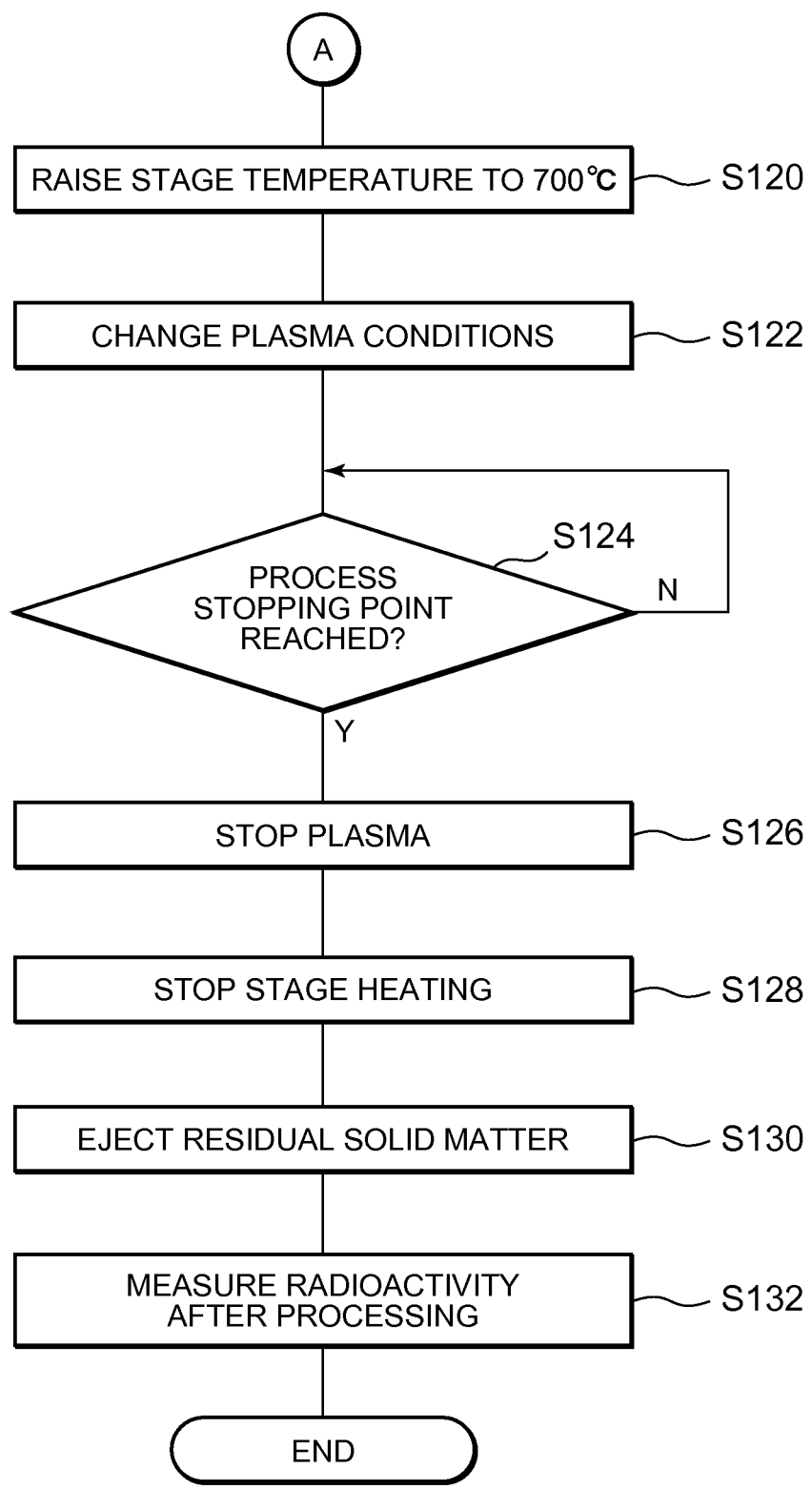
FIG. 6 is a flowchart illustrating a volume reduction processing action implemented by the volume reduction processing system of an embodiment of the invention.

3 Specific Example of Processing Action of Volume Reduction Processing System Next, a specific description will be given, referring to flowcharts, of a processing action of the embodiment. FIG. 5 and FIG. 6 are flowcharts illustrating a volume reduction processing action implemented by the volume reduction processing system 1000 of the embodiment. The drawings referred to thus far will also be referred to as necessary.

On starting the volume reduction process, firstly, a process measuring the initial radioactivity (S102) is executed. In order to do this, the radioactivity meter 102 is utilized. Next, the process stopping point is determined (S104). In order to do this, an action by the process stopping point computation unit 180 is carried out. That is, when using, for example, the weight reduction ratio process stopping point RSP as the process stopping point, the value of the weight reduction target value RT is stored as it is in the process stopping point storage unit 188. When employing the carbon process stopping point CSP as the process stopping point, typically, the accumulation value of carbon containing gas when Expression (2) is taken to be equivalent to the volume reduction target value RT is calculated, and the value is stored in the process stopping point storage unit 188 as the carbon process stopping point CSP. Then, when employing the time process stopping point TSP as the process stopping point, the time process stopping point TSP to which the volume reduction target value RT is typically provided is obtained from the curve 214 (FIG. 2(*b*)) for the same kind of resin measured in advance, and stored in the process stopping point storage unit 188. In the description hereafter, a description will be given assuming that the carbon process stopping point CSP is employed as a typical example.

Next, on the supply side gate valve G1 being opened and the processing target resin 22 of the initially introduced sub-batch (the first sub-batch) supplied, the supply side gate valve G1 is closed again. This, being a process wherein a fixed volume of the processing target resin 22 is supplied by the metering box 124, is a process wherein the processing target resin 22 is placed in advance on the stage 112 of the vacuum receptacle 114 as the first sub-batch. Subsequently, the interior of the vacuum receptacle 114 is depressurized (S106). On reaching a pressure of, for example, around 10 Ton (1.33 kPa), the temperature of the stage 112 is raised to 400° C. by the heater 116 as a process of the first phase (S108). Although the vacuum pump 154 continues a constant exhaust action, pressure is input into the pressure control unit 158 by the pressure sensor 160, and automatically controlled via the degree of opening of the exhaust valve 152.

Continuing, measurement of the carbon dioxide gas concentration by the carbon dioxide sensor 156 is started (S110). The order of the raising of the stage temperature (S108) and the starting of the carbon dioxide gas measurement (S110) may be reversed. Subsequently, the plasma is ignited (S112). Because of this, the supply of a high frequency power to the high frequency coil 142 by the high frequency power source 144 is started. When carrying out this process, the carbon dioxide gas concentration starts to change, as shown at the left end of FIG. 4(*a*). Then, monitoring is carried out to see whether or not the measurement value of the carbon dioxide gas concentration is a maximum value (S114). For example, until the measurement value of the carbon dioxide gas concentration drops from the maximum value to around 90% of the maximum value, it is judged that the measurement value is still the maximum value, and monitoring is continued (N branch of S144). Then, if it is judged that the measurement value has dropped from the maximum value (Y branch of S144), it is determined next whether or not the processing target resin 20 for additional introduction exists (S116). When the sub-batch being processed is the first sub-batch, it is determined whether or not the next second sub-batch exists. If the processing target resin 20 of the sub-batch to be additionally introduced exists (S116,Y branch)), a process adding the processing target resin 20 of the next sub-batch is carried out (S118). The adding process is a process opening the supply side gate valve G1 again and supplying a fixed volume of the processing target resin 20 with the metering box 124, and a process raising the temperature of the stage 112, which has dropped a little from 400° C., to 400° C. again. When the processing target resin 20 of the additional sub-batch does not exist, that is, for example, when sub-batches have been prepared from the first to fourth sub-batch, and the processing target resin 20 being processed is that of the fourth sub-batch (S116, N branch)), no additional introduction is carried out. In the event that processing is to be continued from this condition, the processing of the first phase is completed.

On the processing of the first phase being completed, a condition is such that the carbonized processing target resin 22 is disposed on the stage 112. A process ashing the carbonized processing target resin 22 is carried out in the processing in the second phase. In order to do this, firstly, the temperature of the stage is raised to 700° C. (FIG. 6, S120). Next, the plasma conditions are changed from those of the first phase in accordance with the processing conditions of the second phase (S122). The changes in the plasma conditions include changes in various kinds of conditions, those being a change in the setting of the power from the high frequency power source 144, a change in the flow rate and supply direction of the oxygen gas, and a change in the pressure in the interior of the vacuum receptacle 114 controlled by the pressure control unit 158. On carrying out this process, the accumulation value of the carbon containing gas concentration rises. While the processing is in progress, monitoring is carried out by the computer 182 to see whether or not the processing has reached the process stopping point (S124). In order to do this, the process stopping point stored in the process stopping point storage unit 188 is used. For example, when employing the carbon process stopping point CSP, monitoring is carried out to see whether or not the value of the carbon containing gas accumulation value has reached the process stopping point. As long as the value does not reach the process stopping point (S124, N branch), the monitoring of the value is continued. If the value reaches the process stopping point (S124, Y branch), each of a plasma stopping process (S126), a stage heating stopping process (S128), and a residual solid matter ejection process (S130) is carried out. In order to do this, each of a process stopping the exhaust action of the vacuum receptacle 114, a process stopping the heating power source 120, and a process driving the ejection mechanism 162, is commanded directly by the computer 182, or by the sequence control unit 184. Finally, the radioactivity of the residual solid matter after processing is measured by the extra radioactivity meter 172.

First Embodiment

Modification Example 1

Next, a description will be given of a modification example for increasing the accuracy of determining the process stopping point of the embodiment. In above described Expression (2), the accumulation value of the carbon containing gas concentration is correlated to the volume reduction ratio in a proportional relationship using the proportionality coefficient k. Using a proportional relationship here can be said to implicitly include some assumptions. Firstly, using a proportional relationship means assuming that the speed of exhaust in the exhaust line 150 through the exhaust valve 152 and vacuum pump 154 is constant. Originally, rather than simply accumulating the carbon containing gas concentrations measured by the carbon dioxide sensor 156 during the course of the volume reduction process on the processing target resin 22, it has been necessary to calculate the amount of carbon containing gas concentration generated per unit time, wherein the carbon containing gas concentration is multiplied by the exhaust speed. For the sake of this correction, the exhaust speed is estimated, or a flowmeter is used. It is also possible to correlate the flow rate value of the supplied oxygen gas with the exhaust speed.

One more implicit assumption is included in a conversion of Expression (2). This is an assumption that it is possible to cause all volume reductions by oxidizing oxidized components other than carbon, that is, nitrogen components, sulfur components, and hydrogen components, to be represented by a carbon containing gas such as carbon dioxide. When this assumption is not substantiated, it is not necessarily the case that the process stopping point is determined with sufficient accuracy in a proportional relationship using the proportionality coefficient k. Because of this, it is preferable to improve Expression (2), which uses the coefficient k, in order to determine the process stopping point with higher accuracy.

Figure 7:
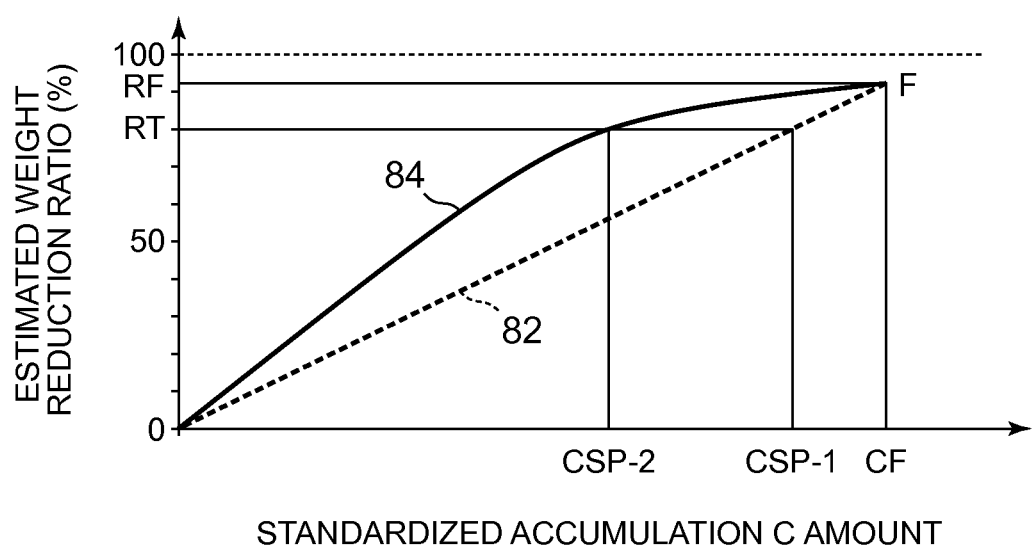
FIG. 7 is an explanatory diagram showing in a graph the relationship between the estimated weight reduction ratio and the accumulation value of carbon dioxide gas concentration before and after a modification in an embodiment of the invention.

As a modification example of the embodiment, a modification is such that the coefficient k is substituted in order to improve the processing accuracy. That is, the coefficient k is taken to be a function corresponding to the accumulation value of carbon dioxide concentration. This point will be described based on FIG. 7. FIG. 7 is an explanatory diagram showing in a graph the relationship between the estimated weight reduction ratio and the accumulation value of carbon dioxide gas concentration before and after the modification. As shown in FIG. 7, the weight reduction ratio when processing is carried out until carbon dioxide gas is no longer emitted is described as corresponding to the mark RF on the vertical axis as the weight reduction ratio corresponding to a point CF of a value at which a value of the accumulation value of carbon dioxide gas concentration divided by dry mass does not become any larger. The horizontal axis is standardized by using the dry mass of the processing target resin 22 before being supplied, and employs a "standardized accumulation C amount", which is (the accumulation value of carbon dioxide gas concentration/dry mass). In this case, attention should be focused on the fact that the estimated weight reduction ratio corresponding to each value on the horizontal axis is expressed as a straight line 82 joining a point F and the origin, in the case of Expression (2), which employs a proportional relationship wherein the coefficient k is a constant.

However, the actual range from the origin to the point CF shown in FIG. 7 covers the processing in the first phase and the processing in the second phase, in which processing conditions such as heating temperature differ widely from each other. Originally, the change in weight reduction ratio reflects conditions in accordance with the more actual progress of the volume reduction process, that is, in which of the first phase and second phase each kind of component—those being carbon components, nitrogen components, sulfur components, and hydrogen components—is more likely to be emitted. Consequently, it can generally be a curve passing through the origin and the point F. Assuming a curve in this way corresponds to the coefficient k of Expression (2) being a function corresponding to the accumulation value of carbon containing gas concentration, rather than a constant. Specifically, according to the studies by the inventor, when the processing target resin 22 is, for example, an ion-exchange resin, a large amount of the nitrogen components, sulfur components, and hydroxyl groups included in the functional group of the ion-exchange resin is emitted in the first phase in comparison with the carbon components. Conversely, more carbon components are ejected in the second phase than in the first phase. This is because the first phase is the carbonization process. When showing one typical example of the relationship between the actual weight reduction ratio value and the standardized accumulation C amount value in this kind of case, the curve is convex, as in a curve 84. This kind of curve actually also depends on the kind of processing target resin, that is, on the resin classification category, and is not always a convex curve. Because of this, by determining a curve corresponding to the curve 84 for each kind of resin of the processing target resin 22, it is possible to determine the relationship between the actual weight reduction ratio value and the standardized accumulation C amount value as a calibration curve. The curve 84 is shown for the sake of the explanation, and is not obtained from the actual processing target resin.

Herein, referring to FIG. 3(b), as the volume reduction target value RT is determined as the weight reduction ratio value, it is possible to plot a point corresponding to the value on the vertical axis of FIG. 7, too. When obtaining the standardized accumulation C amount value corresponding to the volume reduction target value RT using the curve 84, the process stopping point, that is, the carbon process stopping point CSP, is determined as the standardized accumulation C amount value with higher accuracy. A carbon process stopping point CSP-1 when using the curve 82, and a carbon process stopping point CSP-2 when using the curve 84, are shown as the carbon process stopping point CSP in FIG. 7. The inventor predicts that it is when the leeway $\Delta$ (FIG. 3(b)) is set sufficiently small, and the volume reduction target value RT is near the weight reduction ratio RJ at which a discontinuous jump occurs in the total cost, that the difference between the carbon process stopping points CSP-1 and CSP-2 becomes a problem in implementation. As the leeway $\Delta$ can be chosen at a smaller value when employing the carbon process stopping point CSP-2, which is determined with higher accuracy than the carbon process stopping point CSP-1, it is possible to set the volume reduction target value RT to a value nearer to the weight reduction ratio RJ at which a discontinuous jump occurs in the total cost. Because of this, by determining the process stopping point with high accuracy, it is possible to set the volume reduction target value RT to a value advantageous in terms of cost.

It is preferable that the curve 84 is stored in a calibration curve data storage unit 190 (FIG. 1) as a calibration curve for each resin classification category. Ion-exchange resins are classified into a variety of kinds in accordance with, for example, differences in the ratio of anions and cations included in the processing target resin of the ion-exchange resin, the kinds of anion and cation, the processing system in which the ion-exchange resin is used, and the like. The curve 84 corresponding to the classification category of each resin that can at least use the same curve 84 is stored as a calibration curve in the calibration curve data storage unit 190. The process stopping point computation unit 180, in order to determine the process stopping point for the next processing target resin, retrieves the calibration curve data of the resin classification category to which the next processing target resin belongs from the calibration curve data storage unit 190. By so doing, it is possible to determine the process stopping point with an even higher accuracy reflecting the volume reduction process characteristics actually exhibited by the resin of the processing target resin 22.

First Embodiment

Modification Example 2

Finally, a description will be given, as Modification Example 2, of another modification example for determining the process stopping point with high accuracy. As shown in FIG. 1, the processing target resin 20 is supplied by the metering box 124. Because of this, the processing target resin 20 is supplied in constant amounts in accordance with volume rather than mass (weight). Herein, an estimated weight reduction ratio reflecting the amount emitted of carbon contained in gas (Expression (2), FIG. 7) is determined as the ratio between the accumulation value of carbon containing gas concentration and the dry mass. Consequently, when a powder density of the unprocessed processing target resin 20 is provided, it is easier for the process stopping point computation unit 180 to determine the value of Expression (2) or the value on the horizontal axis of FIG. 7. In particular, in order to determine the dry mass, it is preferable to also utilize the moisture regain of the next processing target resin 20. Because of this, the process stopping point computation unit 180 receives powder density data and moisture regain data. The reception of the data may be carried out using communication from some devices, or may be the reception of an input by an operator of the volume reduction processing system 1000. As the process stopping point computation unit 180, by reflecting the powder density and moisture regain, can easily carry out the determination of the dry mass of the next processing target resin of a predetermined volume supplied by the supply mechanism 122, it is possible to reflect the ratio between the accumulation value and dry mass to the determination of the process stopping point.

Heretofore, a specific description has been given of an embodiment of the invention. Each of the heretofore described embodiment and working examples being included in order to explain the invention, the scope of the invention of the application should be fixed based on the claims. Modification examples existing within the scope of the invention are also included in the scope of the claims.

INDUSTRIAL APPLICABILITY

According to the invention, as a volume reduction process whose total cost is reduced becomes possible when considering storage cost too, the invention contributes to a low cost operating of a nuclear power generation facility using an ion-exchange resin.

DESCRIPTION OF REFERENCE NUMERALS AND SIGNS

1000 Volume reduction processing system
20 Processing target resin
22 Supplied processing target resin
102 Radioactivity meter
110 Volume reduction processing device
112 Stage
114 Vacuum receptacle
114R Top wall
116 Heater
118 Stage drive mechanism
120 Heating power source
122 Supply mechanism
124 Metering box
126 Arm
128 Metering box drive mechanism
130 Gas supply line
132 Oxygen canister
134 Regulator valve
142 High frequency coil
144 High frequency power source
150 Exhaust line
152 Exhaust valve
154 Vacuum pump
156 Carbon dioxide sensor
158 Pressure control unit
160 Pressure sensor
162 Ejection mechanism
166 Recovery nozzle
164 Suction pipe
170 Residual solid matter receptacle
172 Extra radioactivity meter
180 Process stopping point computation unit
182 Computer
184 Sequence control unit
188 Process stopping point storage unit
190 Calibration curve data storage unit
202, 204, 214, 404, 414, 84 Curve
302, 304, 82 Straight line
314, 316 Divided straight line
CSP Carbon process stopping point
G1 Supply side gate valve
G2 Ejection side gate valve
P Plasma
RJ Weight reduction ratio at which jump occurs
RT Volume reduction target value
RF Mark
RSP Weight reduction ratio process stopping point
TSP Time process stopping point
Δ Leeway

The invention claimed is:

1. A volume reduction processing system, including:
a radioactivity meter that measures the radioactivity of a processing target resin accompanying a radioactive substance, and outputs radioactivity data or a radioactivity signal indicating the value of the radioactivity;
a volume reduction processing device that carries out a volume reduction process on the processing target resin by carrying out at least one of a heating process on the processing target resin and an oxidation process on the processing target resin itself and gas emitted from the processing target resin using oxygen plasma; and
a process stopping point computation unit that determines a process stopping point for carrying out at least part of the volume reduction process based on a volume reduction target value and the radioactivity data or radioactivity signal,
wherein the volume reduction processing device stops at least one of the heating process and oxidation process when the process stopping point is reached.

2. The volume reduction processing system according to claim 1, further including:
a gas concentration measuring instrument that measures the concentration of a carbon containing gas in at least one of a vacuum receptacle of the volume reduction processing device and an exhaust path from the vacuum receptacle, and outputs concentration data or a concentration signal,
wherein the process stopping point computation unit includes an accumulator unit that calculates an accumulation value of concentrations indicated by the concentration data or concentration signal, and uses the accumulation value for the computation determining the process stopping point.

3. The volume reduction processing system according to claim 2, further including:
a calibration curve data storage unit that stores, for each of a plurality of resin classification categories, calibration curve data relating to the carbon containing gas concentration up to the completion of processing output from the gas concentration measuring instrument,
wherein the process stopping point computation unit, in order to determine the process stopping point for another target resin, retrieves the calibration curve data of the resin classification category to which the another processing target resin belongs from the calibration curve data storage unit.

4. The volume reduction processing system according to claim 3,
wherein the volume reduction processing device includes a supply mechanism that supplies the processing target resin with a predetermined volume as a unit, and
wherein the process stopping point computation unit receives powder density data indicating the powder density of the another processing target resin and moisture regain data indicating the moisture regain of the another processing target resin, determines the dry mass of the another processing target resin of the predetermined volume supplied by the supply mechanism based on the powder density and moisture regain, and employs the ratio between the accumulation value and dry mass to the determination of the process stopping point.

5. The volume reduction processing system according to claim 1, wherein the volume reduction processing device implements a first process oxidizing, with the oxygen plasma, gas emitted from the processing target resin owing to breakdown or carbonization caused by heating the processing target resin to a first temperature, and a second process heating the processing target resin that has passed through the first process to a second temperature, which is a temperature higher than the first temperature, and ashing the processing target resin by breakdown or oxidation of the processing target resin itself with the oxygen plasma.

6. The volume reduction processing system according to claim 5, wherein the process stopping point computation unit sets the process stopping point so as to be positioned in a period during which the second process is being carried out.

7. The volume reduction processing system according to claim 1, further including:

an extra radioactivity meter that measures the radioactivity of a residual solid matter of the processing target resin on which processing has been implemented by the volume reduction processing device as far as the process stopping point, and outputs residual radioactivity data or a residual radioactivity signal.

8. The volume reduction processing system according to claim 1, wherein the volume reduction target value is determined in accordance with a storage class for disposing of or storing the residual solid matter of the processing target resin.

9. The volume reduction processing system according to claim 1, wherein both the heating process and the oxidation process are conducted by the volume reducing processing device.

10. A volume reduction processing method, including the step of:

measuring the radioactivity of a processing target resin accompanying a radioactive substance with a radioactivity meter, and outputting radioactivity data or a radioactivity signal indicating the value of the radioactivity;

carrying out a volume reduction process on the processing target resin by carrying out at least one of a heating process on the processing target resin and an oxidation process on the processing target resin itself and gas emitted from the processing target resin using oxygen plasma, the carrying out step being conducted using a volume reduction processing device;

determining a process stopping point for carrying out at least part of the volume reduction process reduction target value, based on a volume reduction target value and the radioactivity data or radioactivity signal, the determining step being carried out using a stopping point computation unit; and stopping at least one of the heating process and the oxidation process when the process stopping point is reached.

11. The volume reduction processing method according to claim 10, further including:

measuring instrument measuring the concentration of a carbon containing gas in at least one of a vacuum receptacle of the volume reduction processing device and an exhaust path from the vacuum receptacle, and outputting the concentration as concentration data or a concentration signal;

calculating an accumulation value of concentrations indicated by the concentration data or concentration signal; and using the accumulation value for the computation determining the process stopping point.

12. The volume reduction processing method according to claim 11, further including:

storing, for each of a plurality resin classification categories, calibration curve data relating to the carbon containing gas concentration up to the completion of processing output from the gas concentration measuring instrument; and in order to determine the process stopping point for another processing target resin, retrieving the calibration curve data of the resin classification category to which the another processing target resin belongs from the calibration curve data storage unit.

13. The volume reduction processing method according to claim 12, further including:

supplying the processing target resin with a predetermined volume as a unit;

receiving powder density data indicating the powder density of the another processing target resin and moisture regain data indicating the moisture regain of the another processing target resin;

determining the dry mass of the another processing target resin of the predetermined volume supplied by the supply mechanism by reflecting the powder density and moisture regain; and employing the ratio between the accumulation value and dry mass to the determination of the process stopping point.

14. The volume reduction processing method according to claim 10, wherein the carrying out step includes heating the processing target resin to a first temperature; and heating the processing target resin to a second temperature, which is higher than the first temperature, and ashing the processing target resin by a breakdown or oxidation of the processing target resin itself with the oxygen plasma.

15. The volume reduction processing method according to claim 14, further including:

setting the process stopping point so as to be positioned in a period during which the second process is being carried out.

16. The volume reduction processing method according to claim 10, further including:

measuring the radioactivity of a residual solid matter of the processing target resin on which processing has been implemented by the volume reduction processing device as far as the process stopping point, and outputting residual radioactivity data or a residual radioactivity signal.

17. The volume reduction processing method according to claim 10, wherein the volume reduction target value is determined in accordance with a radioactivity category for disposing of or storing the residual solid matter of the processing target resin.

18. The volume reduction processing method according to claim 10, wherein the heating process and the oxidation process are conducted during the carrying out step.

\* \* \* \* \*